United States Patent
Serowski et al.

(10) Patent No.: US 7,278,423 B2
(45) Date of Patent: *Oct. 9, 2007

(54) SWIVEL DEVICE UTILIZING BEARING CLEARANCE TO ALLOW CARBON DIOXIDE LADEN EXHAUST

(75) Inventors: Andrew Serowski, Plantsville, PA (US); John Raymond Pujol, Murrysville, PA (US); Jeffrey Kenneth Anthony Fusaro, Pittsburgh, PA (US); Timothy Gabriel Holloran, Pittsburgh, PA (US)

(73) Assignee: RIC Investments, LLC., Wilmington, DE (US)

( * ) Notice: Subject to any disclaimer, the term of this patent is extended or adjusted under 35 U.S.C. 154(b) by 814 days.

This patent is subject to a terminal disclaimer.

(21) Appl. No.: 10/642,964

(22) Filed: Aug. 18, 2003

(65) Prior Publication Data

US 2004/0035419 A1 Feb. 26, 2004

Related U.S. Application Data

(63) Continuation of application No. 09/337,595, filed on Jun. 21, 1999, now Pat. No. 6,615,830, which is a continuation of application No. 08/810,332, filed on Feb. 27, 1997, now Pat. No. 5,937,851.

(51) Int. Cl.
*A62B 9/04* (2006.01)

(52) U.S. Cl. .............................. 128/202.27; 128/205.24

(58) Field of Classification Search ........... 128/202.27, 128/205.11, 205.25, 205.24, 206.21, 207.12, 128/911, 912

See application file for complete search history.

(56) References Cited

U.S. PATENT DOCUMENTS

| | | | |
|---|---|---|---|
| 3,906,996 A | 9/1975 | Depass et al. | |
| 3,977,432 A | 8/1976 | Vidal | |
| 4,150,071 A | 4/1979 | Pecina | |
| 4,463,755 A | 8/1984 | Suzuki | |
| 4,621,634 A | 11/1986 | Nowacki et al. | |
| 4,637,384 A | 1/1987 | Schroeder | |
| 4,794,921 A | 1/1989 | Lindkvist | |
| 4,909,248 A | 3/1990 | McLennan Anderson | |
| 4,944,310 A | 7/1990 | Sullivan | |
| 4,967,744 A | 11/1990 | Chua | |
| 5,002,050 A | 3/1991 | McGinnis | |
| 5,036,847 A | 8/1991 | Boussignac et al. | |
| 5,284,160 A | 2/1994 | Dryden | |
| 5,320,092 A | 6/1994 | Ryder | |
| RE35,339 E | 10/1996 | Rapoport | |
| 5,662,101 A | 9/1997 | Ogden et al. | |
| 5,778,872 A | 7/1998 | Fukunaga et al. | |
| 5,937,851 A * | 8/1999 | Serowski et al. | 128/202.27 |
| 5,983,896 A | 11/1999 | Fukunaga et al. | |
| 6,615,830 B1 * | 9/2003 | Serowski et al. | 128/202.27 |

* cited by examiner

*Primary Examiner*—Teena Mitchell
(74) *Attorney, Agent, or Firm*—Michael W. Haas

(57) ABSTRACT

A swivel exhaust conduit for rotatably connecting a patient mask to the delivery conduit of a positive pressure air supply. The swivel exhaust conduit design provides an exhaust port that utilizes the rotating bearing of the swivel conduit's rotating two-piece design for permitting and directing exhaust of $CO_2$ laden air. A baffle chamber formed in the clearance of the two pieces provides an area where noise is reduced. As $CO_2$ laden exhaust exits the swivel exhaust conduit, it is directed away from the patient mask and down the outside of the delivery conduit via a slit pattern on the swivel conduit.

10 Claims, 6 Drawing Sheets

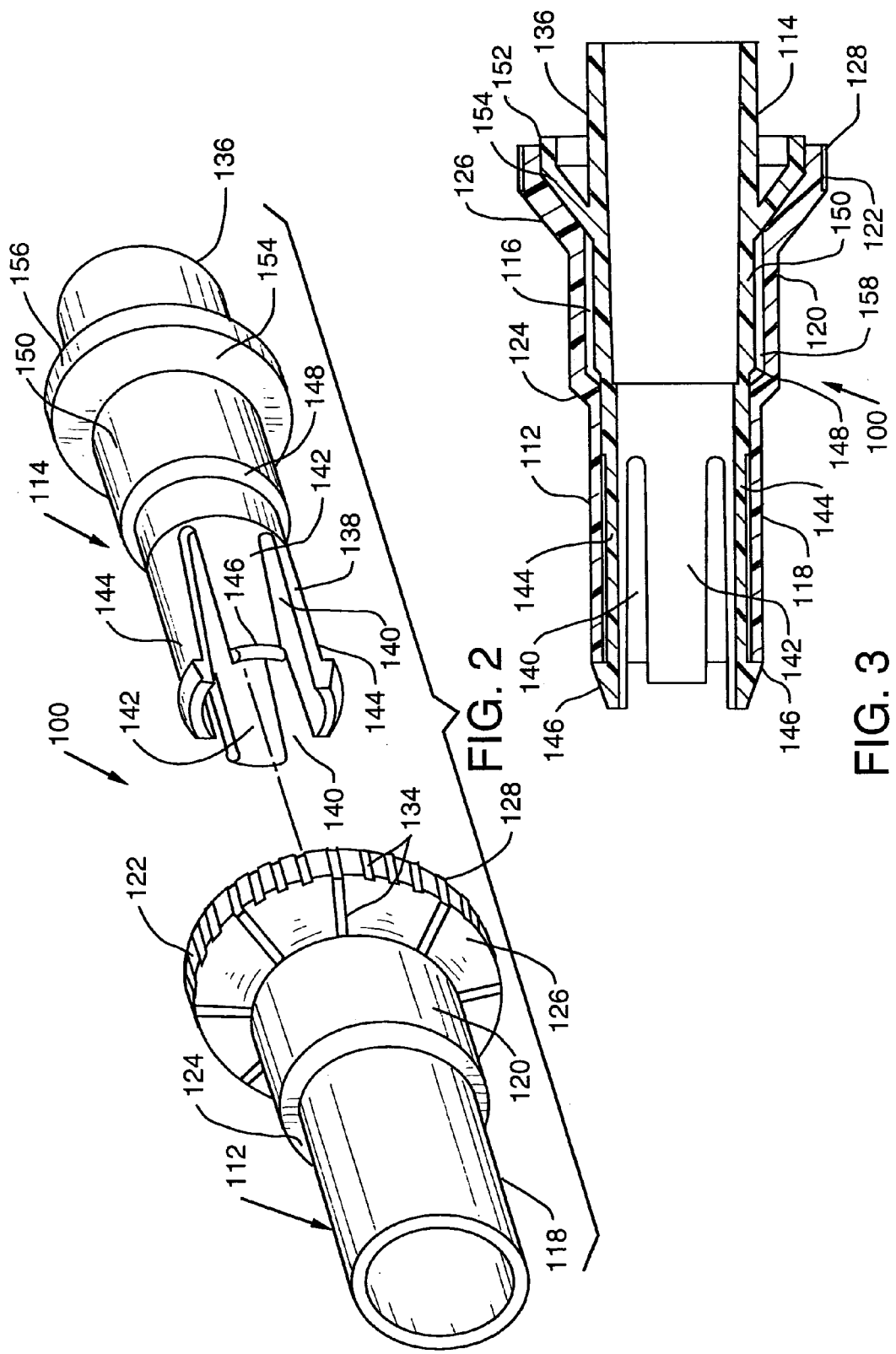

SWIVEL DEVICE UTILIZING BEARING CLEARANCE TO ALLOW CARBON DIOXIDE LADEN EXHAUST

CROSS-REFERENCE TO RELATED APPLICATIONS

This application claims priority under 35 U.S.C. § 120 as a Continuation of U.S. patent application Ser. No. 09/337,595 filed Jun. 21, 1999 now U.S. Pat. No. 6,615,830, which is a Continuation of U.S. patent application Ser. No. 08/810,332 filed Feb. 27, 1997, now U.S. Pat. No. 5,937,851.

FIELD OF INVENTION

The present invention relates to providing a respiratory mask with a two-piece swivel conduit that uses the rotating bearing of its swivel design to permit and preferably direct carbon dioxide ($CO_2$) laden exhaust from the patient breathing circuit.

BACKGROUND OF THE INVENTION

A variety of delivery systems are known that deliver gas at positive pressure for consumption by the user. The uses and applications of such systems vary. Some such systems have been developed for the treatment of sleep apnea.

Sleep apnea syndrome is an episodic upper airway obstruction during sleep. As a consequence, there is repeated interruption of sleep in the patient. Positive airway pressure (PAP) devices have been developed to treat this disorder. A typical PAP device comprises a flow generator (e.g., a blower) which delivers gas via a delivery conduit to a patient interface, such as a mask.

Several types of respiratory face masks for delivering gas to a patient are known. One such mask incorporates ports in the body of the mask to provide an exhaust leak to purge the system of $CO_2$ laden air. However, several drawbacks are associated with ports in the body of the mask. For example, air exiting the mask ports may create noise or blow on the patient, causing discomfort.

Respironics, Inc. of Murrysville, Pa. has developed and manufactured a swivel conduit having exhaust vents under the name Whisper Swivel® Exhalation Port. See FIG. 1a. This two-piece swivel conduit not only provides a swivel connection between the mask and the delivery conduit but also includes a plurality of downwardly directed exhaust slits. The slit configuration of the vents acts to reduce noise and direct the $CO_2$ laden exhaust away from the patient.

SUMMARY OF THE INVENTION

The improved swivel conduit rotatably connects a patient mask to the delivery conduit of the present invention of a positive pressure air supply. The improved design provides an exhaust vent for purging the system of $CO_2$ laden air that utilizes the rotating bearing of its two-piece design. A baffle chamber in the design reduces the intensity of the sound generated. As $CO_2$ laden exhaust exits the swivel conduit, it is directed away from the patient mask and down the outside of the delivery conduit via a slit pattern on the swivel conduit. The unique two-peice bearing design may be easily disassembled for cleaning.

The swivel conduit design directs $CO_2$ laden expiratory exhaust away from the patient in a diffused air flow stream along the delivery conduit. This diffused air flow provides for a less perceptible sensation to the patient or sleeping partner.

BRIEF DESCRIPTION OF THE DRAWINGS

The invention will become more readily apparent from the following description of preferred embodiments thereof shown, by way of example only, in the accompanying drawings, wherein:

FIG. 2 is an exploded perspective view of the swivel conduit device according to a first embodiment of the present invention;

FIG. 3 is a cross-sectional view of the swivel conduit according to the first embodiment of the present invention;

DETAILED DESCRIPTION OF THE INVENTION

Figure 1A:
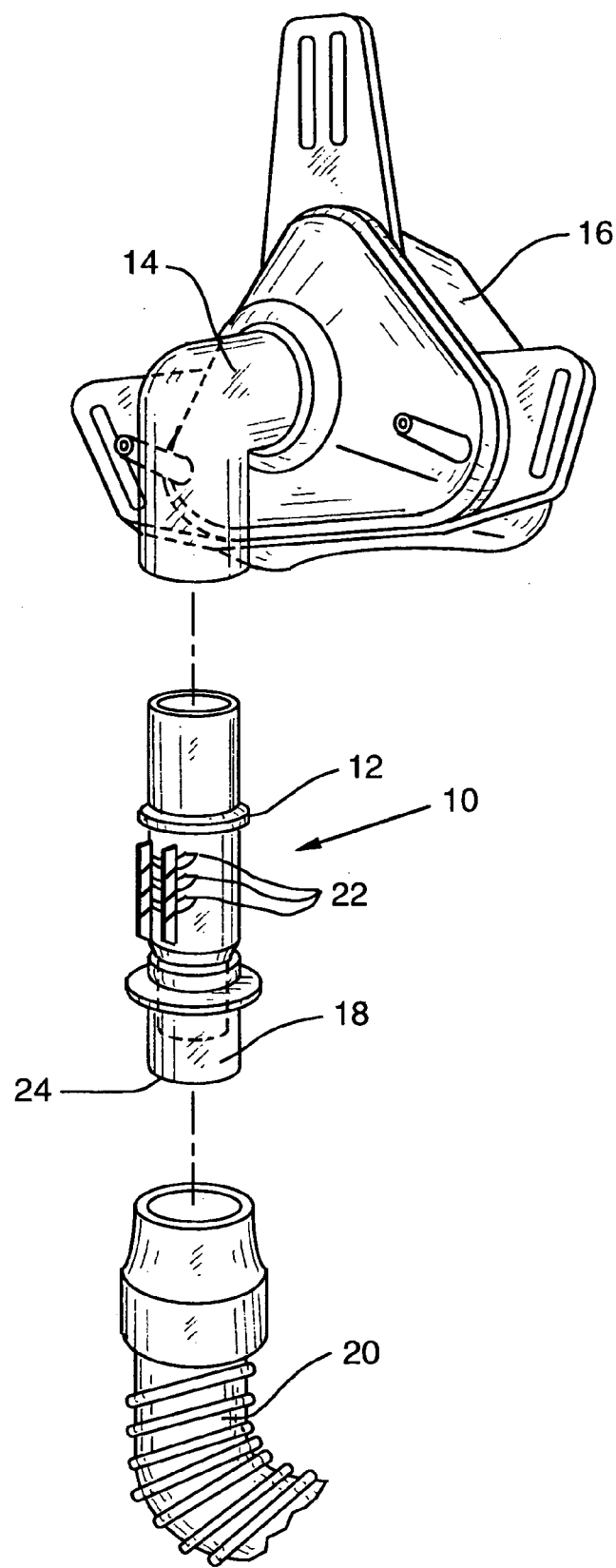
FIG. 1a is an exploded perspective view of a Whisper Swivel® device assembled with a respiratory mask and delivery conduit.
Figure 1B:
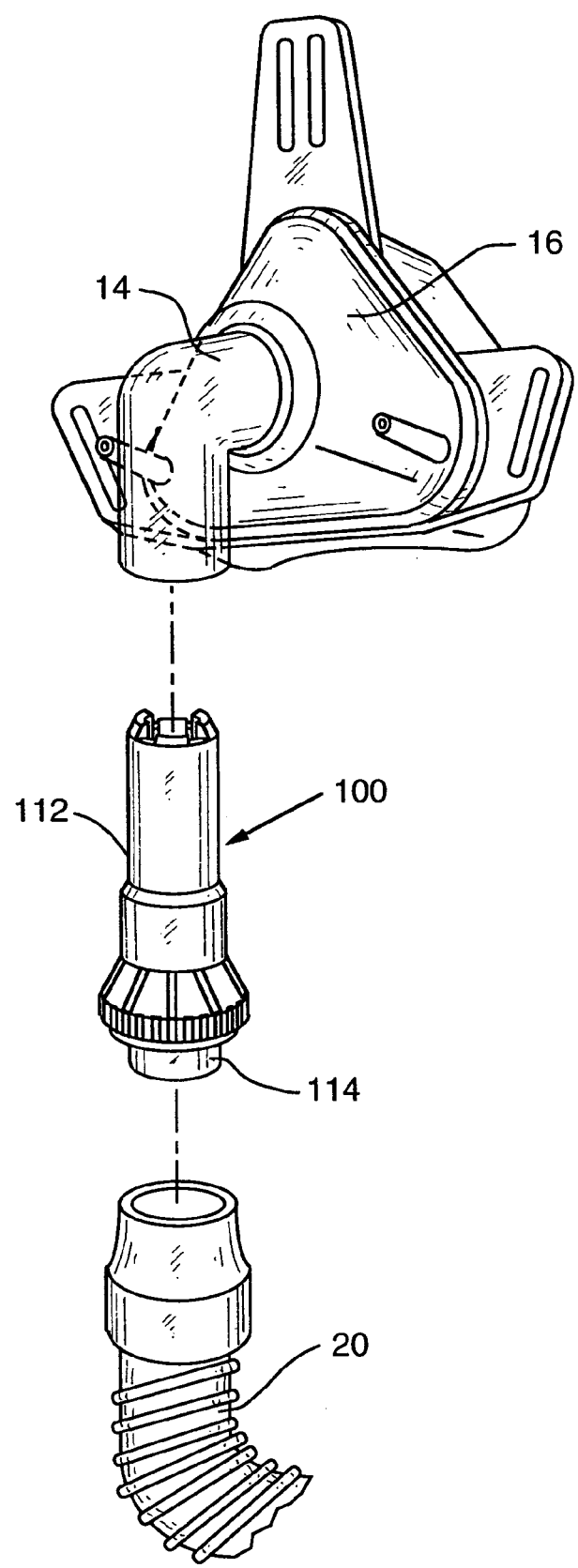
FIG. 1b is an exploded perspective view of a swivel conduit according to a first embodiment of the present invention assembled with a respiratory mask and delivery conduit.

There is generally indicated at 10 in FIG. 1 a swivel conduit of conventional Whisper Swivel® Exhalation Port device manufactured by Respironics, Inc. Swivel conduit 10 has a mask connection piece 12, which is received within one end of an L-shaped conduit 14 attached to a respiratory mask 16, and a delivery conduit piece 18, which is received within one end of a delivery conduit 20, to deliver pressurized air from a positive airway pressure device or other ventilatory device (not shown). A plurality of parallel slits 22 on the mask connection piece 12 are directed downwardly towards the delivery conduit end 24 of the swivel conduit 10 to permit purging of $CO_2$ laden expiratory exhaust. The mask connection piece 12 and the delivery conduit piece 18 are rotatably coupled to each other, thus, allowing the mask 16 to rotate relative to the delivery conduit 20.

FIGS. 1b, 2, 3 and 4 illustrate a first embodiment of an improved swivel exhaust device 100. The improved two-piece design has a mask connection piece 112, which is received within one end of an L-shaped mask conduit 14, and a delivery conduit piece 114, which is received within one end of the delivery conduit 20. The mask connection piece 112 and the delivery conduit piece 114 are rotatably coupled to each other. Discharge of $CO_2$ laden expiratory exhaust is permitted through the clearance 116 between the mask connection piece 112 and the delivery conduit piece 114.

Figure 4:
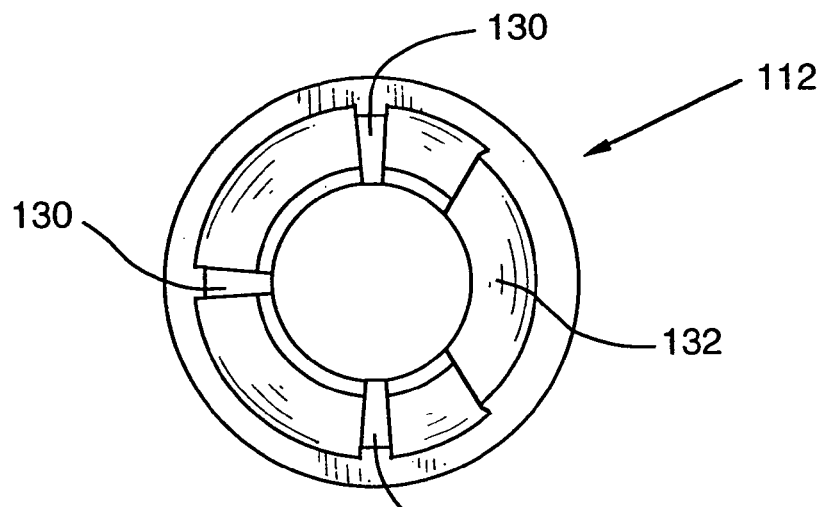
FIG. 4 is top plan view of the mask connection piece according to the first embodiment of the present invention.

The mask connection piece 112 generally comprises a tubular mask connection end 118 which is received in the L-shaped mask conduit 14, an intermediate stepped portion 120 having a larger diameter than the mask connection end 118, and a radial exhaust end 122 opposite the mask connection end 118. The stepped portion 120 is joined to the mask connection 118 end by a sloped portion 124 whose diameter increases from the mask connection end diameter to that of the stepped portion diameter. The exhaust end 122 also has a sloped portion 126 in which the diameter increases to that of an annular portion 128 having a diameter larger than the stepped portion diameter. This design of the mask connection piece 112 helps direct $CO_2$ laden exhaust out and away from the device 100. Raised portions 130 on the interior surface of the sloped portion 126 and annular portion 128 of the exhaust end 122 form a slit pattern which further directs $CO_2$ laden exhaust away from the patient (FIG. 4). There are preferably three narrower raised portions 130 and one wider raised portion 132. As $CO_2$ laden exhaust exits the device 100, it is directed away from the patient mask 16 via the slit pattern down the outside of the delivery conduit 20. In use, the wider raised portion 132 can be positioned nearest the patient side of the mask connection piece 112 so that $CO_2$ laden exhaust is directed away from the patient.

The exterior surface of the sloped 126 and annular 128 portions of the exhaust 122 end have raised serrations 134 to prevent intentional blocking of the $CO_2$ laden exhaust. However, the exterior surface in the preferred embodiment is formed without the serrations 134.

The delivery conduit piece 114 includes a tapered delivery conduit 136 end, which is received within the delivery conduit 20, and a swivel connection end 138, which is rotatably received within the mask connection end 118 of the mask connection piece 112. The swivel connection end 138 preferably has four longitudinal slots 140 forming four retaining arms 142, 144. Two of the retaining arms 144 that are opposite each other preferably are longer than the other two retaining arms 142. All four arms 142, 144 have radial outwardly projecting segments 146 to retain the delivery conduit piece 114 within the mask connection piece 112. By pressing inwardly on the radial segments 146 of the two longer retaining arms 144, the mask connection piece 112 and the delivery conduit piece 114 may be easily separated. The delivery conduit piece 114 has a locating portion 148 joining an intermediate stepped portion 150 and the swivel connection end 138, and an exhaust portion 152 disposed between the stepped portion 150 and the delivery conduit end 136. When the two pieces 112, 114 are assembled, the two longer retaining arms 144 form cantilever springs which load, center and locate the sloped portion 124 of the stepped portion of the mask connection piece 112 against the locating portion 148 of the delivery conduit piece 114.

The exhaust portion 152 of the delivery conduit piece comprises a sloped portion 154 of increasing diameter and an annular portion 156 of a diameter larger than the stepped portion diameter. The area between the stepped portions 120, 150 of the mask connection piece 112 and the delivery conduit piece 114 forms a baffle chamber 158 through which the $CO_2$ laden exhaust flows. The baffle chamber 158 gradually reduces the noise of the $CO_2$ laden exhaust being purged from the device 100.

Figure 5:
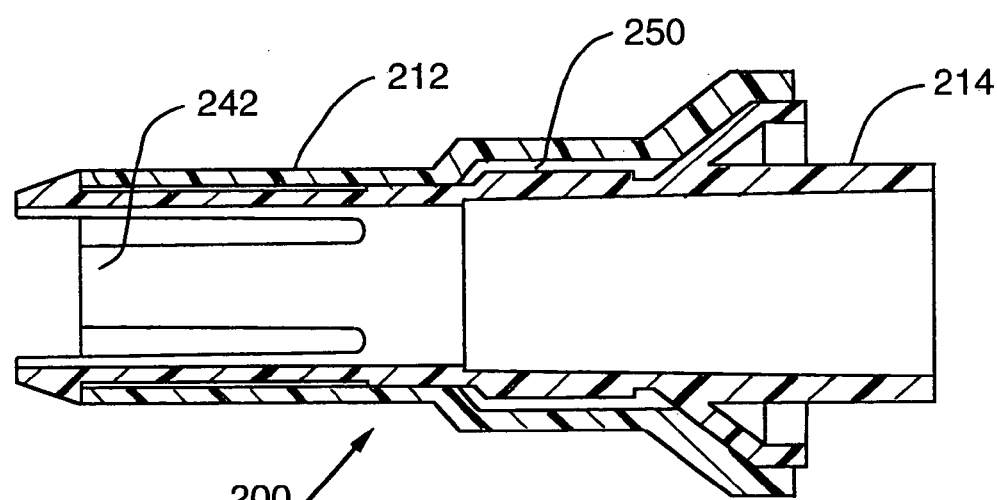
FIG. 5 is a cross-sectional view of the swivel conduit according to a second embodiment of the present invention.
Figure 6:
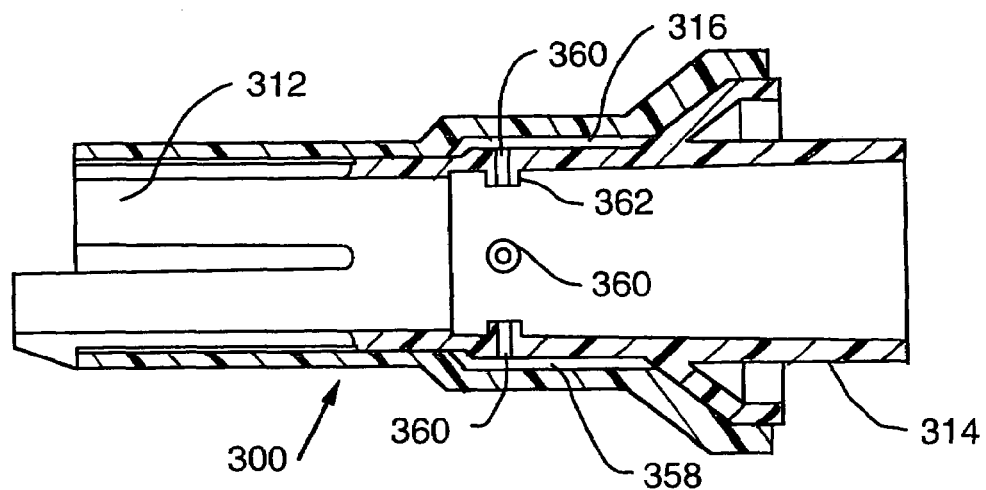
FIG. 6 is a cross-sectional view (rotated 45° as compared to FIG. 5) of the swivel conduit according to a third embodiment of the present invention.
Figure 7:
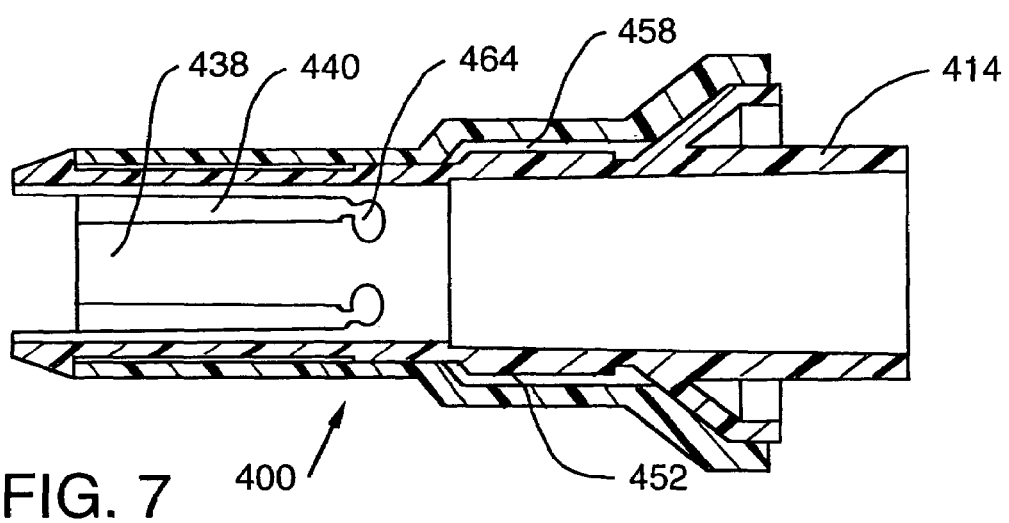
FIG. 7 is a cross-sectional view of the swivel conduit according to a fourth preferred embodiment of the present invention.

Alternative embodiments are shown in FIGS. 5-8 with the embodiment of FIG. 7 being the preferred embodiment. Like elements will be designated by like reference numerals.

A swivel conduit 200 in accordance with a second embodiment of the present invention is shown in FIG. 5. In this embodiments, the stepped portion of the delivery conduit piece 214 includes a raised baffle 250 to reduce noise. In this embodiment, as well as in the embodiments illustrated in FIGS. 6 and 7, the two shorter retaining arms 242 preferably do not have radial segments. Alternately, in an unillustrated embodiment, all retaining arms are the same longer length with the two arms which are pressed inwardly for disassembly having locating notches.

A swivel conduit 300 in accordance with a third embodiment of the present invention is shown in FIG. 6. In this embodiment1 spaced radial holes 360 are provided (preferably four) in the stepped portion 350 of the delivery conduit piece 314 to provide an additional path for $CO_2$ laden exhaust between the interior of the delivery conduit piece 314 and the baffle chamber 358. Hole bosses 362 protrude inwardly to divert fluids or secretions around the holes. In this embodiment, $CO_2$ laden exhaust flow is determined by both the holes 360 and the clearance 316 between the mask connection piece 312 and the delivery conduit piece 314.

In a swivel conduit 400 of a fourth preferred embodiment illustrated in FIG. 7 of the present invention, the delivery conduit piece 414 includes a baffle portion 452 as described in accordance with FIG. 5. Also, each of the longitudinal slots 440 of the swivel connection end 438 ends in a hole 464. These holes 464 are preferably angled for manufacturing purposes but could be disposed radially. These holes 464 provide an improved exhaust entrance to the baffle chamber 458.

Figure 8:
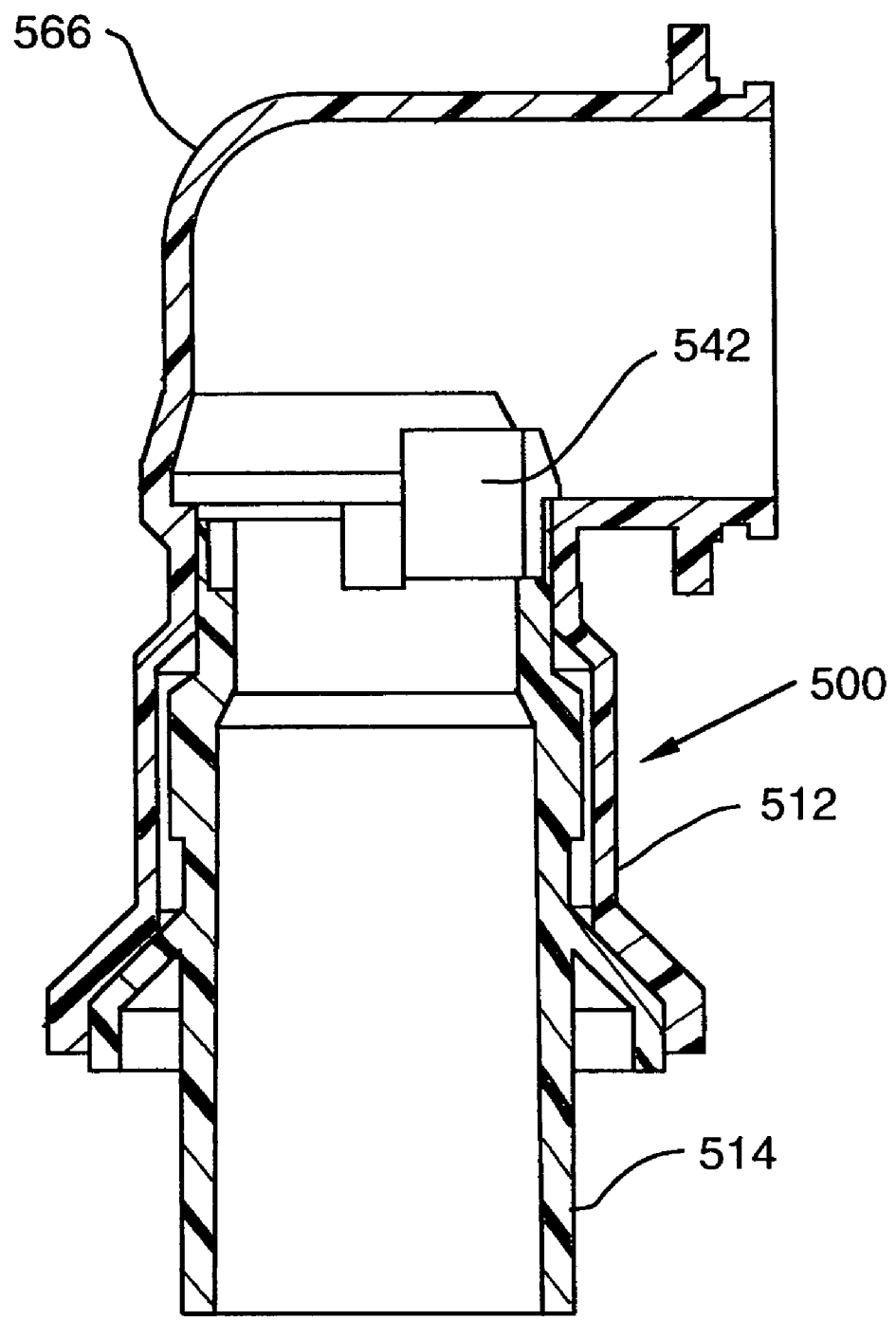
FIG. 8 is a cross-sectional view of the swivel conduit according to a fifth embodiment of the present invention.

In a fifth embodiment 500 of the present invention illustrated in FIG. 8, the mask connection piece 512 also comprises an L-shaped portion 566 for attachment to the respiratory mask 16, thus, reducing the need for a separate L-shaped conduit 14. In this design, a single retaining arm 542 attaches the pieces 512 and 514 together. Likewise, it is contemplated that the delivery conduit piece 514 could be unitarily formed with the delivery conduit 20.

The present invention provides several advantages over that of the prior art. Its unique design provides optimum comfort through improved exhaust rates and reduced noise. The pieces, which can be formed by injection molding1 do not require additional processing, thus reducing manufacturing costs. The two-piece design is easily disassembled for cleaning and discourages exhaust vents from being sealed off. The swivel action also allows for the unplugging of secretions.

Although the invention has been described in detail for the purpose of illustration, it is to be understood that such detail is solely for that purpose and that variations can be made therein by those skilled in the art without departing from the spirit and scope of the invention as it may be limited by the claims.

What is claimed is:

1. An exhaust assembly for use with a breathing gas delivery system including a delivery conduit and a patient interface, the exhaust assembly comprising:
   a first member associated with a patient interface;
   a second member adapted to be coupled to a delivery conduit, and wherein the first member and the member portion couple together such that a chamber is defined between the first member and the second member;
   a first opening at least partially defined by the first member communicating the chamber with ambient atmosphere; and
   a second opening defined in a side wall of the second member communicating an interior of the exhaust assembly with the chamber, wherein an exhaust flow path is defined from the interior of the exhaust assembly to ambient atmosphere via the first opening and the second opening, and wherein the exhaust flow path is continuously open.

2. The exhaust assembly of claim 1, wherein the first opening is a gap between the first member and the second member.

3. The exhaust assembly of claim 1, wherein the second opening is further defined by a slot provided in the second member.

4. The exhaust assembly of claim 1, wherein the second opening is defined by a hole provided in the second member.

5. The exhaust assembly of claim 1, wherein the second opening is at least one of a plurality of radial holes defined around a perimeter of the second member.

6. A connector for use with a breathing gas delivery system including a delivery conduit and a patient interface, the connector comprising:
   a first member associated with a patient interface; and
   a second member adapted to be coupled to a delivery conduit, wherein the first member and the second member couple together to define an exhaust flow path from an interior of the first member or the second member to ambient atmosphere, and wherein the exhaust flow path is continuously open.

7. A connector according to claim 6, wherein the first member and the second member are selectively detachable from one another.

8. A connector according to claim 6, wherein first member and the second member are rotatable relative to one another about a common axis.

9. A connector according to claim 6, wherein the exhaust flow path communicates with an interior of the connector via an opening defined in side wall of the second member, and wherein the exhaust flow path communicates with ambient atmosphere via a gap between the first member and the second member.

10. A connector according to claim 6, wherein the exhaust flow path communicates with an interior of the connector via a plurality of openings defined in a side wall of the second member, and wherein the exhaust flow path communicates with ambient atmosphere via a gap provided between the first member and the second member.

* * * * *